(12) United States Patent
Yu

(10) Patent No.: US 11,445,987 B2
(45) Date of Patent: Sep. 20, 2022

(54) X-RAY COLLIMATOR, X-RAY DETECTOR SYSTEM AND CT DEVICE

(71) Applicant: Neusoft Medical Systems Co., Ltd., Liaoning (CN)

(72) Inventor: Jun Yu, Shenyang (CN)

(73) Assignee: Neusoft Medical Systems Co., Ltd., Liaoning (CN)

( * ) Notice: Subject to any disclaimer, the term of this patent is extended or adjusted under 35 U.S.C. 154(b) by 57 days.

(21) Appl. No.: 17/215,657

(22) Filed: Mar. 29, 2021

(65) Prior Publication Data

US 2021/0298698 A1    Sep. 30, 2021

(30) Foreign Application Priority Data

Mar. 30, 2020    (CN) .......................... 202010238041.X

(51) Int. Cl.
| | |
|---|---|
| *A61B 6/06* | (2006.01) |
| *B33Y 80/00* | (2015.01) |
| *A61B 6/03* | (2006.01) |
| *A61B 6/00* | (2006.01) |

(52) U.S. Cl.
CPC ............... *A61B 6/06* (2013.01); *A61B 6/032* (2013.01); *A61B 6/4233* (2013.01); *B33Y 80/00* (2014.12)

(58) Field of Classification Search
CPC .. A61B 6/08; A61B 6/06; G11B 7/131; G11B 2007/0013; G11B 7/1376; G11B 7/1398; G02B 27/30; G02B 6/32; G02B 27/0172; G02B 26/123; G02B 27/0081; G02B 27/0944; G02B 6/002; G02B 6/0016; G02B 5/005; G02B 6/0045; G02B 6/0033; G02B 2006/12107; G02B 6/0058; G02B 21/241; G02B 23/105; G02B 6/285; A61N 5/1065; G21K 1/02; G21K 1/04; G21K 1/046; G21K 5/04; G21K 1/062; G01N 2223/316
See application file for complete search history.

(56) References Cited

U.S. PATENT DOCUMENTS

2007/0258566 A1    11/2007    Eckenbach

FOREIGN PATENT DOCUMENTS

| CN | 1409326 A | 4/2003 |
|---|---|---|
| CN | 1707699 A | 12/2005 |
| CN | 101221824 A | 7/2008 |
| CN | 100416707 C | 9/2008 |
| CN | 1975938 B | 8/2012 |

(Continued)

*Primary Examiner* — Don K Wong
(74) *Attorney, Agent, or Firm* — Fish & Richardson P.C.

(57) ABSTRACT

A collimator includes a collimator body formed by 3D printing technology and one or more side plates formed by non-3D printing technology. The collimator body includes first through holes, body side walls, and openings located on at least one side of the collimator body. The first through holes and the openings are enclosed by respective body side walls, extend through the collimator body, and are arranged in an array. The one or more side plates have a thickness smaller than a thickness of the body side walls, and are connected with the at least one side of the collimator body to constitute second through holes together with the openings. Each through hole has a square-frustum-like shape with extension lines intersecting at a focus of an emission source of X rays, such that the X-rays pass through the through hole.

20 Claims, 8 Drawing Sheets

(56) References Cited

FOREIGN PATENT DOCUMENTS

| CN | 202802548 U | * | 3/2013 |
|---|---|---|---|
| CN | 103876767 A | | 6/2014 |
| CN | 104605877 B | | 5/2017 |

* cited by examiner

X-RAY COLLIMATOR, X-RAY DETECTOR SYSTEM AND CT DEVICE

CROSS REFERENCE TO RELATED APPLICATIONS

This application claims priority to Chinese Patent Application No. 202010238041X entitled "X-RAY COLLIMATOR, X-RAY DETECTOR SYSTEM AND CT DEVICE" filed on Mar. 30, 2020, the entire content of which is incorporated herein by reference.

TECHNICAL FIELD

The present disclosure relates to medical devices and in particular to an X-ray collimator, an X-ray detector system and a computed tomography (CT) device.

BACKGROUND

With the development of computed tomography (CT), a CT detector system has more and more slices, resulting in more and more corresponding detector pixel units. In order to facilitate production and increase finished product rate, the detector is generally divided into a plurality of detector modules along an X direction. These detector modules are arranged along an arc concentric with a focus of an emission source (e.g., an X-ray bulb tube). Each detector module is divided into a plurality of detector sub-modules along a Z direction according to the number of desired slices. In order to ensure consistent characteristics of the detectors, the detector sub-modules in the detector module are usually arranged along an arc in the Z direction, so that the distances from the focus to the detector modules and thus sub-modules are consistent and the radiation attenuation characteristics are consistent, thereby facilitating subsequent image processing.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

One aspect of the present disclosure features an X-ray collimator including: a collimator body formed by three-dimensional (3D) printing; and one or more side plates formed by non-3D printing. The collimator body includes: a plurality of first through holes, a plurality of body side walls, and a plurality of openings located on at least one side of the collimator body. The plurality of first through holes and the plurality of openings are enclosed by respective body side walls, extend through the collimator body, and are arranged in an array. The one or more side plates have a thickness smaller than a thickness of the body side walls. The one or more side plates are connected with the at least one side of the collimator body to constitute a plurality of second through holes together with the plurality of openings, the first through holes and the second through holes constituting a plurality of through holes of the X-ray collimator. Each through hole of the plurality of through holes has a square-frustum-like shape with extension lines of four lateral edges intersecting at a focus of an emission source of X-rays, such that the X-rays pass through the through hole.

In some embodiments, the one or more side plates include one or more trapezoidal side plates, one or more side plates with a U-shaped section, one or more side plates with an L-shaped section, or a combination thereof according to a number of sides of the collimator body on which the openings are disposed, and the U-shaped section or the L-shaped section is parallel to a top surface of the collimator body.

In some embodiments, four sides of the collimator body are provided with the openings and the one or more side plates include one side plate.

In some embodiments, the openings are disposed on at least two adjacent sides of the collimator body, and at least two side plates adjacent to each other are disposed; for each two adjacent side plates, protrusions are disposed at intervals on joining edges of the two adjacent side plates, grooves are formed between adjacent protrusions, and protrusions on an edge of one of the two adjacent side plates are located in grooves of a joining edge of the other one of the two adjacent side plates, and the protrusions of the two adjacent side plates are alternately distributed to form a splicing seam.

In some embodiments, four sides of the collimator body are provided with the openings, the one or more side plates include one side plate, protrusions are disposed on opposite edges of the side plate, grooves are formed between adjacent protrusions, protrusions of one of the opposite edges are located in grooves of the other one of the opposite edges, and the protrusions of the opposite edges are alternately distributed to form a splicing seam.

In some embodiments, two opposite sides of the collimator body are provided with the openings, protrusions located at respective two opposite ends of the two opposite sides and grooves located between the protrusions, the one or more side plates include two side plates with protrusions disposed at intervals on respective two opposite edges of the two side plates, protrusions of each of the two side plates are located in the grooves of the collimator body, and the protrusions of the two side plates and the protrusions of the collimator body are alternately arranged.

In some embodiments, each of the protrusions has a trapezoid-like shape or a square-like shape.

In some embodiments, the collimator body has a square-frustum-like shape, and the splicing seam is located at a lateral edge of the collimator body.

In some embodiments, the one or more side plates include: at least two side plates, where, for each two adjacent side plates, a width of protrusions of an edge of one of the two adjacent side plates is equal to a thickness of the other one of the two adjacent side plates with an edge joined with the edge of the one of the two adjacent side plates, or only one side plate, where the width of the protrusions is equal to the thickness of the side plate. Each of the protrusions can have a trapezoid-like shape or a square-like shape.

In some embodiments, the collimator body has a square-frustum-like shape, and the splicing seam and a lateral edge of the collimator body are spaced. Each of the protrusions can have a trapezoid-like shape or a square-like shape. Each of the protrusions can have the trapezoid-like shape, and longer bases of the protrusions can be located at an outermost side of the one or more side plates.

In some embodiments, the thickness of the one or more side plates is equal to or smaller than ½ of the thickness of the body side walls.

In some embodiments, a height of the one or more side plates is greater than a height of the collimator body, and when the X-ray collimator is mounted on a detector sub-module, the one or more side plates block at least part of the detector sub-module.

In some embodiments, the thickness of each of the body side walls decreases gradually from a bottom surface of the collimator body to a top surface of the collimator body.

In some embodiments, the non-3D printing includes rolling or sheet metal bending.

Another aspect of the present disclosure features an X-ray detector system including: a plurality of detector sub-modules and a plurality of X-ray collimators. Each of the plurality of X-ray collimators is mounted on a different corresponding detector sub-module of the plurality of detector sub-modules, and the plurality of X-ray collimators and the plurality of detector sub-modules are spliced along at least one of a first direction or a second direction of the X-ray detector system. Each of the X-ray collimators includes: a collimator body formed by three-dimensional (3D) printing and one or more side plates formed by non-3D printing. The collimator body includes: a plurality of first through holes, a plurality of body side walls, and a plurality of openings located on at least one side of the collimator body. The plurality of first through holes and the plurality of openings are enclosed by respective body side walls, extend through the collimator body, and are arranged in an array. The one or more side plates have a thickness smaller than a thickness of the body side walls. The one or more side plates are connected with the at least one side of the collimator body to constitute a plurality of second through holes together with the plurality of openings, the first through holes and the second through holes constituting a plurality of through holes of the X-ray collimator. Each through hole of the plurality of through holes has a square-frustum-like shape with extension lines of four lateral edges intersecting at a focus of an emission source of X-rays, such that the X-rays pass through the through hole.

In some embodiments, for each of the X-ray collimators, the openings are disposed on at least two adjacent sides of the collimator body, and at least two side plates adjacent to each other are disposed; for each two adjacent side plates, protrusions are disposed at intervals on joining edges of the two adjacent side plates, grooves are formed between adjacent protrusions, and protrusions on an edge of one of the two adjacent side plates are located in grooves of a joining edge of the other one of the two adjacent side plates, and the protrusions of the two adjacent side plates are alternately distributed to form a splicing seam.

In some embodiments, for each of the X-ray collimators, four sides of the collimator body are provided with the openings, the one or more side plates include one side plate, protrusions are disposed on opposite edges of the side plate, grooves are formed between adjacent protrusions, protrusions of one of the opposite edges are located in grooves of the other one of the opposite edges, and the protrusions of the opposite edges are alternately distributed to form a splicing seam.

In some embodiments, for each of the X-ray collimators, two opposite sides of the collimator body are provided with the openings, protrusions located at respective two opposite ends of the two opposite sides and grooves located between the protrusions, the one or more side plates include two side plates with protrusions disposed at intervals on respective two opposite edges of the two side plates, protrusions of each of the two side plates are located in the grooves of the collimator body, and the protrusions of the two side plates and the protrusions of the collimator body are alternately arranged.

In some embodiments, the collimator body has a square-frustum-like shape, and the splicing seam is located at a lateral edge of the collimator body. The one or more side plates include: at least two side plates, where, for each two adjacent side plates, a width of protrusions of an edge of one of the two adjacent side plates is equal to a thickness of the other one of the two adjacent side plates with an edge joined with the edge of the one of the two adjacent side plates, or only one side plate, where the width of the protrusions is equal to the thickness of the side plate.

In some embodiments, the collimator body has a square-frustum-like shape, and the splicing seam and a lateral edge of the collimator body are spaced.

In some embodiments, the thickness of the one or more side plates is equal to or smaller than ½ of the thickness of the body side walls.

In some embodiments, for each of the X-ray collimators, a height of the one or more side plates is greater than a height of the collimator body, and when the X-ray collimator is mounted on a corresponding detector sub-module, the one or more side plates block at least part of the detector sub-module.

A further aspect of the present disclosure features a computed tomography (CT) device including: a bulb tube emitting X-rays and an X-ray detector system. The X-ray detector system includes: a plurality of detector sub-modules and a plurality of X-ray collimators configured to collimate the X-rays. Each of the plurality of X-ray collimators is mounted on a different corresponding detector sub-module of the plurality of detector sub-modules, and the plurality of X-ray collimators and the plurality of detector sub-modules are spliced along at least one of a first direction or a second direction of the X-ray detector system. Each of the X-ray collimators includes: a collimator body formed by three-dimensional (3D) printing and one or more side plates formed by non-3D printing. The collimator body includes: a plurality of first through holes, a plurality of body side walls, and a plurality of openings located on at least one side of the collimator body. The plurality of first through holes and the plurality of openings are enclosed by respective body side walls, extend through the collimator body, and are arranged in an array. The one or more side plates have a thickness smaller than a thickness of the body side walls. The one or more side plates are connected with the at least one side of the collimator body to constitute a plurality of second through holes together with the plurality of openings, the first through holes and the second through holes constituting a plurality of through holes of the X-ray collimator. Each through hole of the plurality of through holes has a square-frustum-like shape with extension lines of four lateral edges intersecting at a focus of an emission source of X-rays, such that the X-rays pass through the through hole.

The exemplary embodiments will be described in detail here, and examples thereof are illustrated in the accompanying drawings. When the following description refers to the accompanying drawings, unless otherwise stated, the same reference signs in different drawings designate the same or similar elements. The implementation manners described in the following exemplary embodiments do not represent all implementation manners consistent with the present application. On the contrary, they are merely examples of devices and methods consistent with some aspects of the present application as defined in the appended claims.

DETAILED DESCRIPTION

Figure 1:
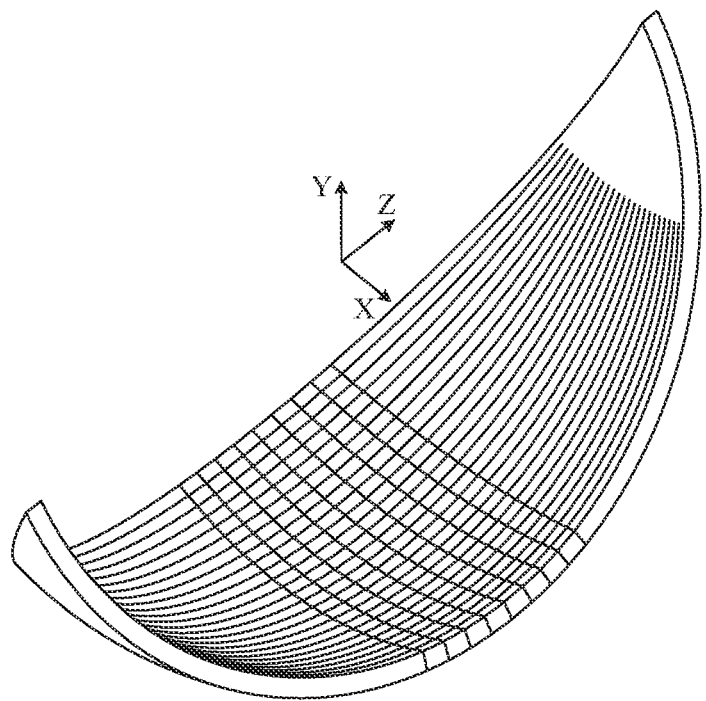
FIG. 1 is a schematic diagram of spherical division of a detector according to an example of the present disclosure.

Because detector sub-modules are arranged along arcs concentric with a focus along an X direction and a Z direction respectively, receiving faces of scintillators of the detector sub-modules are equivalent to being arranged on a spherical surface. Based on the spherical division of a detector in FIG. 1, it can be known that detector modules are mounted onto a fixing support and arranged along an arc along an X-direction to form a detector system of CT. Thus, it is inevitable that a splicing seam may exist between the detector modules. A plurality of detector sub-modules are arranged on a module support along a Z direction to form a detector module. Therefore, it is also inevitable that a splicing seam may exist between the detector sub-modules. From the viewpoint of data collection and image reconstruction, it is desired that pixels of different detector sub-modules are consistent in both effective area and inter-pixel seam, thereby facilitating maintaining the accuracy of image information and improving image quality.

In a detector system of a CT device, an X-ray collimator (hereinafter referred to as grid) is disposed above a scintillator to absorb scattered rays of the X-rays. As a width of the detector gradually increases, higher requirements are proposed for the grid in the Z direction as well as in the X direction. As a result, blocking layers for absorbing the scattered rays are also arranged in the Z direction. A grid having the blocking layers in X and Z directions at the same time can be referred to as a 2D grid. At present, the 2D grid may be manufactured by sheet metal bending, insert splicing or casting. Along with the progress of 3D printing technology, a 2D grid manufactured by 3D printing technology emerges. However, a side wall of the 2D grid manufactured by 3D printing technology has a limited wall thickness which may reach a minimum of about 0.1 mm. A thickness of the splicing position of the side walls of two adjacent grids can be excessively large. Therefore, when collimators manufactured by 3D printing technology are adopted, a larger seam is to be reserved between the detector modules and/or the detector sub-modules for smooth assembly. It is noted that the splicing seam between the detector modules and/or the detector sub-modules intensively contributes to a pixel size tolerance and an assembly error of the detector modules and the detector sub-modules.

Implementations of the present disclosure can solve the above problem. In some implementations, a collimator includes a collimator body manufactured by 3D printing technology and one or more side plates manufactured by non-3D printing technology and the one or more side plates has a thickness smaller than a thickness of a body side wall of the collimator body. This configuration is equivalent to that the one or more side plates replace all the side walls of a collimator manufactured by 3D printing technology. In this case, when the detector sub-modules or the detector modules are spliced, it is unnecessary to reserve a larger seam between the detector modules or the detector sub-modules. Thus, pixels of different detector sub-modules are consistent in both the effective area and the inter-pixel seam. Further, the one or more side plates are connected to at least one side of the collimator body to constitute a plurality of second through holes of the collimator together with respective openings and serve as the at least one side wall of the collimator body. Therefore, sides of the collimator are in a closed state (for example, the four sides are all connected with the one or more side plates or the opposite sides along the X direction are connected with the one or more side plates). Thus, the four sides of the collimator are not fragile and cannot be easily subjected to damage or poor accuracy. Detailed descriptions will be made below to the X-ray collimator, the X-ray detector system and the CT device of the present disclosure.

Figure 2:
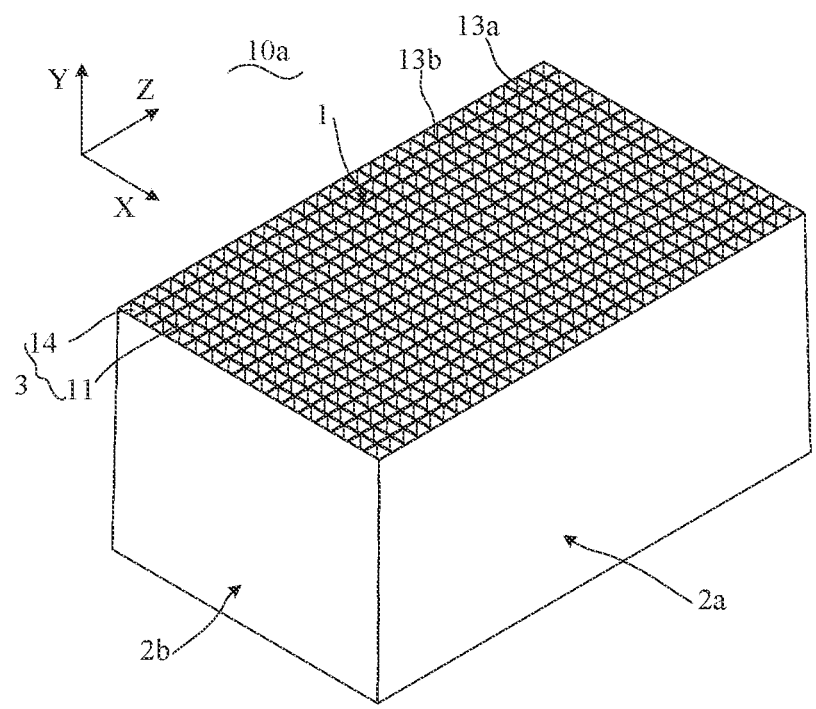
FIG. 2 is a structural schematic diagram of a collimator according to an example of the present disclosure.
Figure 3:
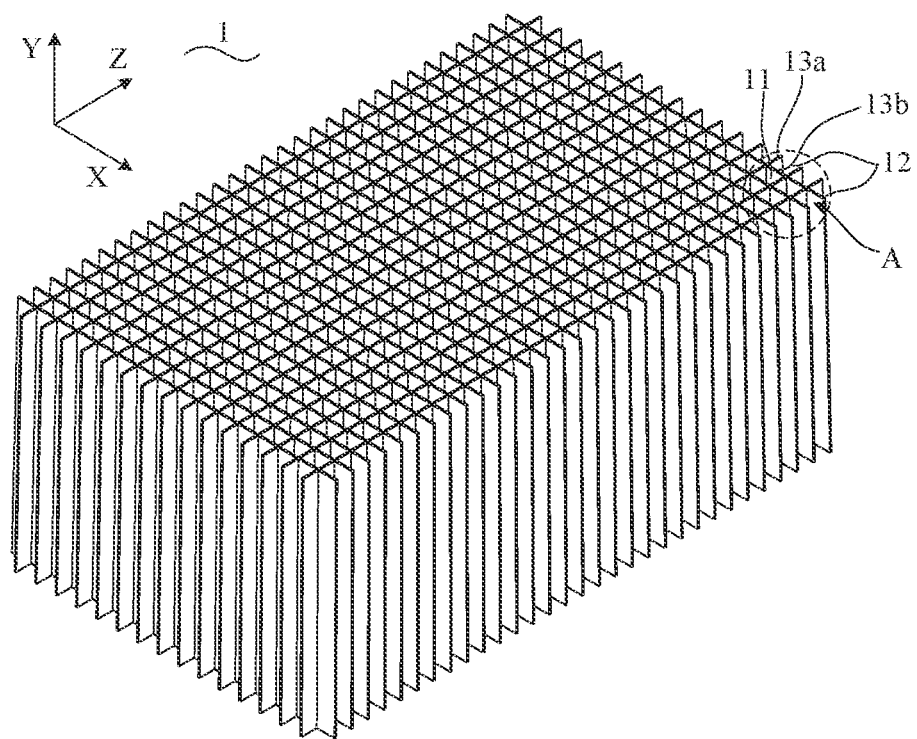
FIG. 3 is a structural schematic diagram of a collimator body of the collimator shown in FIG. 2.
Figure 4:
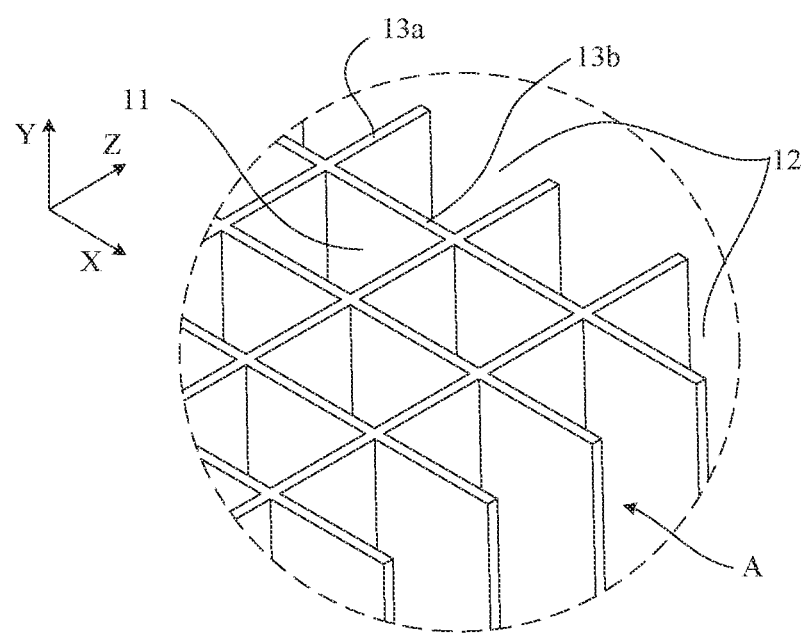
FIG. 4 is a partial enlarged view of portion A shown in FIG. 3.
Figure 6:
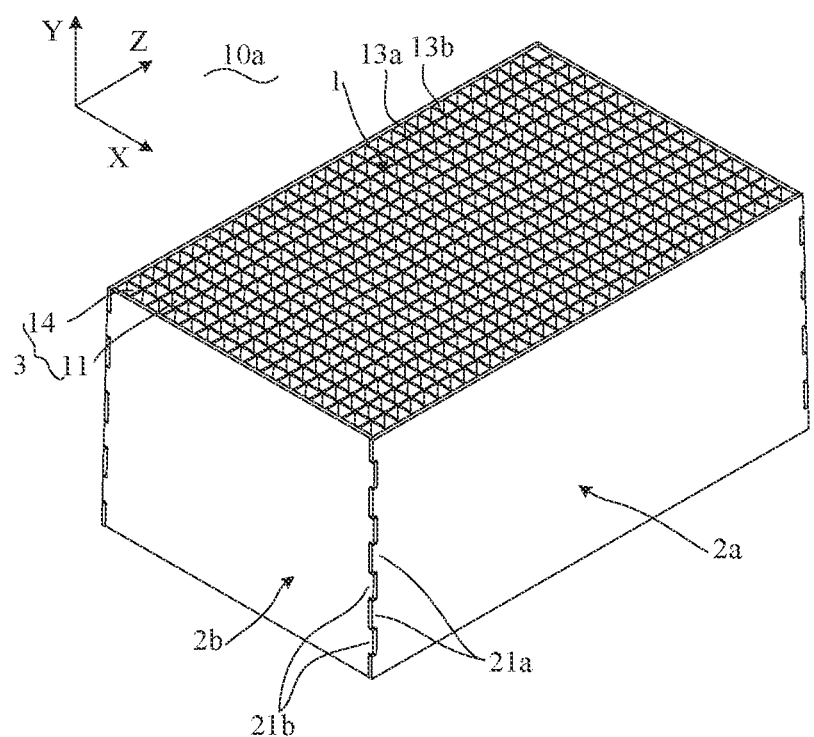
FIG. 6 is a structural schematic diagram of a collimator according to an example of the present disclosure.
Figure 9:
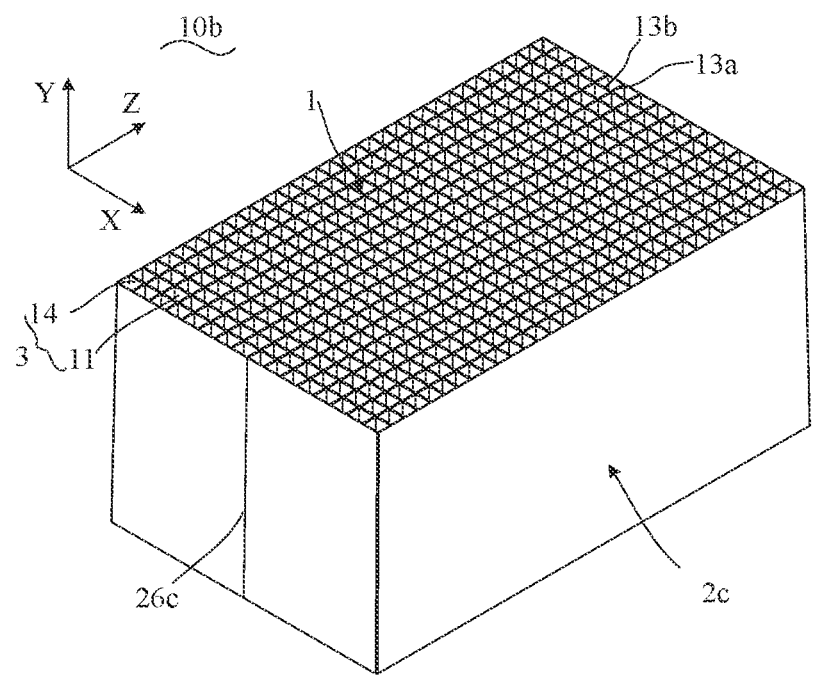
FIG. 9 is a structural schematic diagram of a collimator according to an example of the present disclosure.
Figure 12:
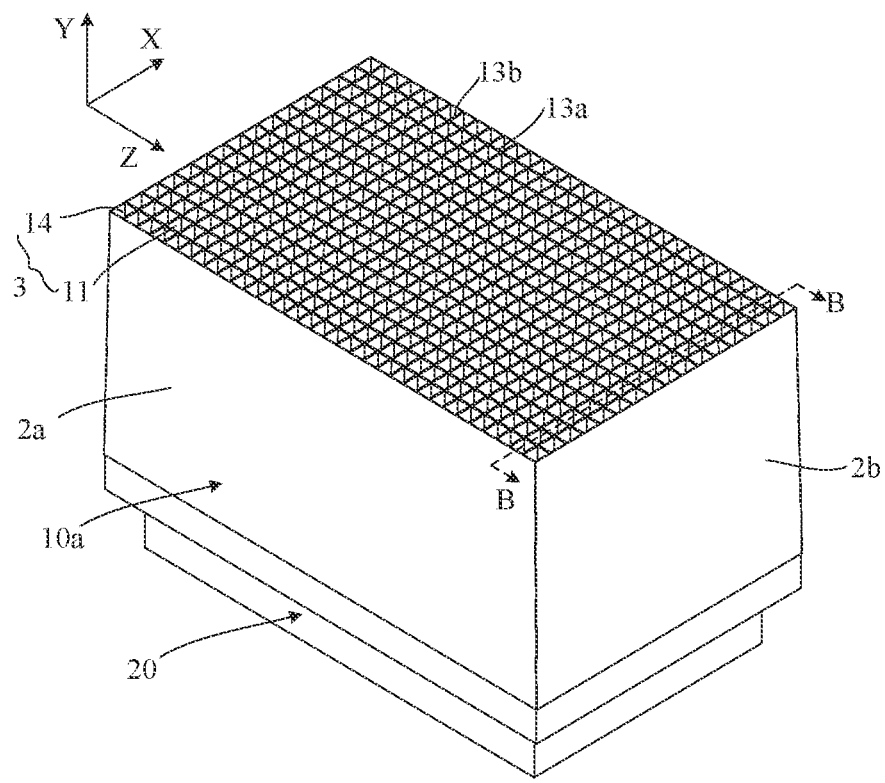
FIG. 12 is a structural schematic diagram of a collimator mounted on a detector sub-module according to an example of the present disclosure.

With reference to FIGS. 2, 6, and 12, the present disclosure provides a collimator 10a, including a collimator body 1, and side plates 2a and 2b. With reference to FIG. 9, the present disclosure provides another collimator 10b including a collimator body 1 and a side plate 2c. The collimator bodies 1 of the collimators 10a and 10b are of the same structure. A material of the collimator body 1 may be a high X-ray attenuation material such as tungsten or molybdenum. In some examples, as shown in FIGS. 3 and 4, the collimator body 1 is formed by 3D printing technology and includes a plurality of first through holes 11, a plurality of body side walls 13a and 13b, and a plurality of openings 12 located on at least one side of the collimator body 1. The plurality of first through holes 11 and the plurality of openings 12 are enclosed by respective body side walls 13a and 13b (the body side walls along a Z direction are denoted as 13a and the body side walls along an X direction are denoted as 13b), extend through the collimator body 1 and are arranged in an array, for example, an array of 16×16 or 32×16. In FIG. 3, an array of 32×16 is shown. In some examples, as shown in FIGS. 3 and 4, the plurality of openings 12 are disposed on four sides of the collimator body 1. Therefore, each first through hole 11 are enclosed by four body side walls (two body side walls 13a and two body side walls 13b), the openings 12 located at four corners of the array are enclosed by two body side walls (one body side wall 13a and one body side wall 13b), and other openings 12 are enclosed by three body side walls (one body side wall 13a and two body side walls 13b or two body side walls 13a and one body side wall 13b). Which side of the collimator body 1 is provided with the openings 12 is dependent on a position of a detector sub-module corresponding to the collimator body 1 in the entire detector system.

Figure 11:
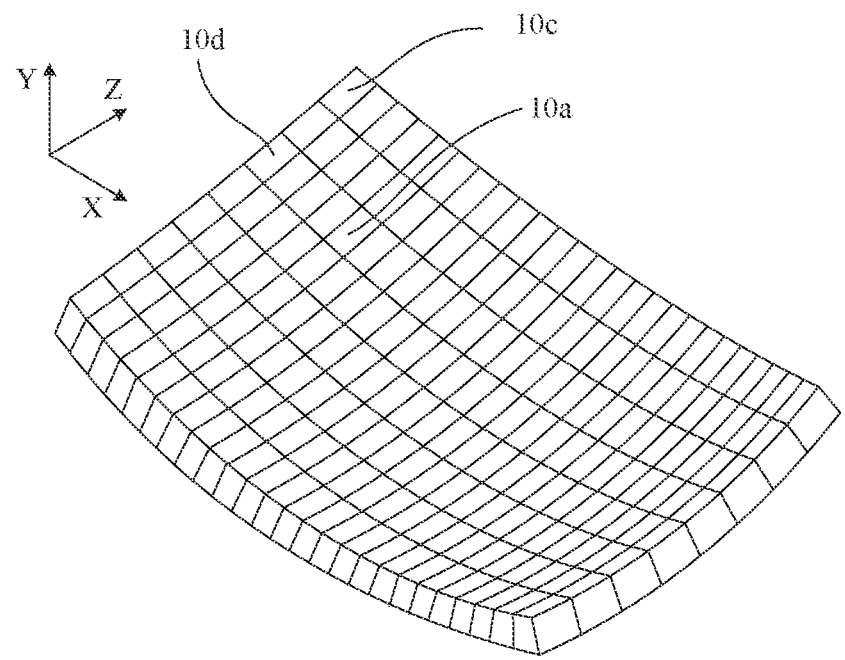
FIG. 11 is a schematic diagram of distribution of collimators in a part of an X-ray detector system according to an example of the present disclosure.

As shown in FIG. 11, the collimator 10a is to be spliced with four adjacent collimators, that is, spliced in both X and Z directions and thus the openings 12 are formed on the four sides of the collimator body 1; a collimator 10c is to be spliced with adjacent collimators via two sides and thus the openings 12 are formed on the two sides of the collimator body 1; and a collimator 10d is to be spliced with three adjacent collimators and thus the openings 12 are formed on three adjacent sides of the collimator body 1. In some examples, when a collimator does not need to be spliced with adjacent collimators along the Z direction, the openings 12 are to be formed on the opposite sides of the collimator along the X direction. In this case, the two sides of the collimator body 1 along the Z direction include the body side walls formed by 3D printing technology. From the viewpoint of production simplification, only two types of collimator bodies 1 may be formed: the first collimator body 1 is to be spliced in both Z and X directions and thus the openings 12 are formed on the four sides of the first collimator body 1 as shown in FIG. 3; the second collimator body 1 is to be spliced only in the X direction, and thus the openings 12 are formed on the opposite sides of the collimator along X direction and the sides along the Z direction are integrally formed with the collimator body 1 by 3D printing technology.

With reference to FIGS. 2, 6, 8A, 8B, 9 and 12 and in combination with FIGS. 3 and 4, the side plates 2a, 2b and 2c have a thickness smaller than the thickness of the body side walls 13a and 13b. The side plates 2a, 2b and 2c can be manufactured by non-3D printing technology, and be connected to at least one side of the collimator body 1 to constitute a plurality of second through holes 14 together with the openings 12. All the first through holes 11 and all the second through holes 14 constitute through holes 3 of the collimator.

The one or more side plates 2a, 2b, and 2c are fixed on the collimator body by bonding. A material of the side plates 2a, 2b and 2c may be a high X-ray attenuation material such as tungsten or molybdenum. In some examples, the thickness of the side plates 2a, 2b and 2c is equal to or smaller than ½ of the thickness of the body side walls 13a and 13b.

Each through hole 3 of the collimator is shaped like square frustum, and extension lines of four lateral edges of the through hole intersect at a focus of an emission source of the X-rays so that the X-rays pass through the through hole 3. Referring to FIG. 3, in some cases, the thickness of each of the body side walls 13a and 13b gradually decreases from a bottom surface of the collimator body 1 to a top surface of the collimator body 1, thereby realizing a non-equal wall thickness design. In this way, the formed through hole 3 is more approximate to a standard square frustum, thereby improving shielding effect. In some cases, the thickness of each of the body side walls 13a and 13b can be constant from bottom to top.

In some examples, the one or more side plates include one of a trapezoidal side plate, a side plate with a U-shaped section, a side plate with an L-shaped section, or a combination thereof according to the number of the sides of the collimator body 1 on which the openings 12 are disposed. The section is parallel to the top surface of the collimator body. It is noted that those skilled in the art may understand that the arrangement of the side plates is not limited to the following implementations and any combinations of the manners in which the side plates are disposed according to the number of the sides on which openings 12 are disposed shall all fall within the scope of the present disclosure. Specifically, the one or more side plates may be disposed in the following manners:

1) In a case that the four sides of the collimator body 1 are all provided with the openings 12, the arrangement may include the following manners: 1.1) as shown in FIGS. 2, 6 and 12, in an implementation, the four sides of the collimator body 1 are connected with one trapezoidal side plate respectively and the four side plates serve as the side walls of the collimator body 1. Note that the arrangement can also include but not limited to one or more of the following manners in addition to the above manner: 1.2) one trapezoidal side plate is spliced with one side plate with a U-shaped section; 1.3) one trapezoidal side plate is spliced with two side plates with an L-shaped section; 1.4) two side plates with a U-shaped section are spliced together; 1.5) four side plates with an L-shaped section are spliced together; 1.6) one side plate with a U-shaped section is spliced with two side plates with an L-shaped section; and 1.7) two side plates with an L-shaped section are spliced together.

2) In a case that three sides of the collimator body 1 are provided with the openings 12, the arrangement includes but not limited to one or more of the following manners: 2.1) three trapezoidal side plates are spliced together; 2.2) one trapezoidal side plate is spliced with two side plates with an L-shaped section; 2.3) one side plate with a U-shaped section is arranged; 2.4) two side plates with an L-shaped section are spliced together; and 2.5) one trapezoidal side plate is spliced with one side plate with an L-shaped section.

3) In a case that two sides of the collimator body 1 are provided with the openings 12, the arrangement includes but not limited to one or more of the following manners: 3.1) in a case that two opposite sides are provided with the openings 12 (namely, in a case that splicing is only in the X direction), each side is connected with one trapezoidal side plate; 3.2) in a case that two adjacent sides are provided with the openings 12 respectively, the following manners can be implemented: 3.2.1) the one or more side plates include one side plate with an L-shaped section; and/or 3.2.2) the one or more side plates include two trapezoidal side plates, each of which is connected to one side of the collimator.

4) In a case that one side of the collimator body 1 is provided with the openings 12, the one or more side plates include one trapezoidal side plate.

Figure 10:
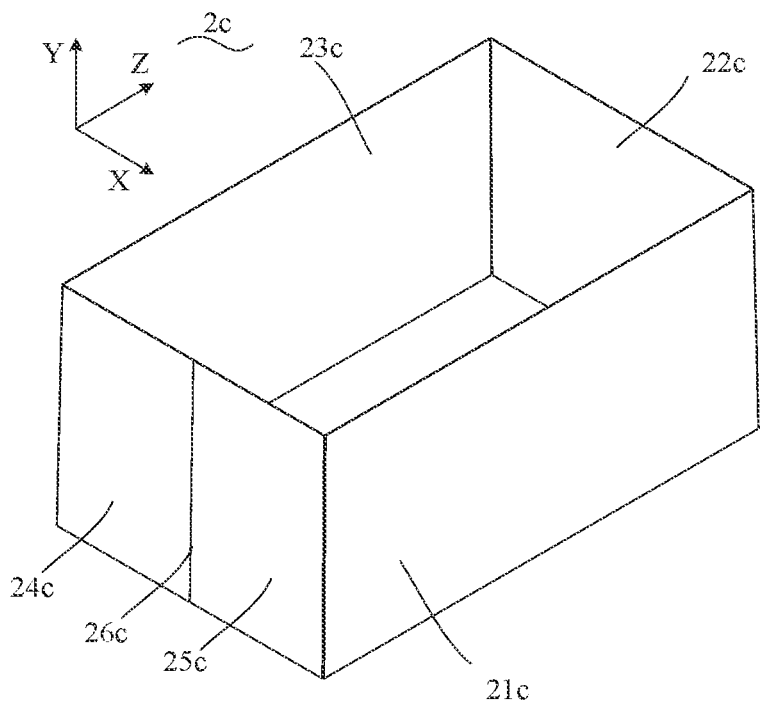
FIG. 10 is a structural schematic diagram of a side plate of the collimator shown in FIG. 9.

Furthermore, in one implementation, when the four sides of the collimator body 1 are all provided with the openings 12, only one side plate may be disposed as shown in FIGS. 9 and 10. The side plate denoted as 2c is bent into a hollow square frustum and may be divided into a first side plate 21c, a second side plate 22c, a third side plate 23c, a fourth side plate 24c and a fifth side plate 25c with bent round corners as demarcation lines.

Figure 5:
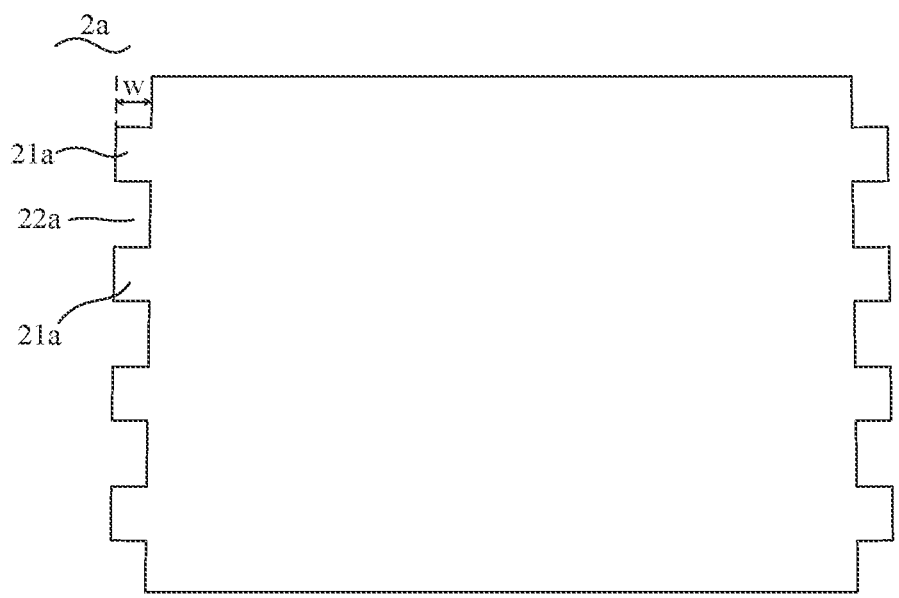
FIG. 5 is a structural schematic diagram of a side plate of a collimator according to an example of the present disclosure.

In some implementations, a splicing seam of two side plates or a splicing seam of the opposite edges of one side plate may be connected by a process such as adhesive bonding or laser welding. In another implementation, as shown in FIGS. 5 and 6, to ensure accurate positioning and mutual supporting of the side plates of the collimator, and thus the good accuracy and stable structure of the collimator, when there are at least two side plates, for example, two side plates 2a along the Z direction and two side plates 2b along the X direction in FIG. 6, two adjacent side plates 2a and 2b may include protrusions 21a and 21b disposed at intervals on their respective edges and a groove, for example, a groove 22a shown in FIG. 5, is formed between two adjacent protrusions. In FIG. 5, to highlight the shape of the protrusion, the protrusion 21a of the side plate 2a is depicted on a larger scale, which does not limit the true size of the protrusion relative to the side plate. In the adjacent side plates 2a and 2b, the protrusions of one side plate are located in the grooves of the other side plate so that the adjacent side plates 2a and 2b are engaged via the alternately distributed protrusions to form a splicing seam. In some implementations, as shown in FIG. 6, the side of the collimator body 1 along the X direction and the side of the collimator body 1 along the Z direction are two adjacent sides forming a lateral edge. In the direction from the bottom surface to the top surface of the collimator body 1, the protrusions of the adjacent side plates 2a and 2b are alternately distributed on the lateral edge in an order of protrusion 21a, protrusion 21b, protrusion 21a and protrusion 21b, so as to form a splicing seam.

In the above implementation, the four side plates are connected to the sides of the collimator body 1 respectively to form four splicing seams. When the openings 12 are disposed on all four sides of the collimator body 1, only one side plate may be disposed and a shape of the side plate after bending can be identical to that of the collimator body 1. In this case, there can be only one splicing seam. Protrusions are disposed on the opposite edges of the side plate, and a groove is formed between two adjacent protrusions. The protrusions of one edge are located in the grooves of the other edge so that the alternately distributed protrusions and grooves of the opposite edges are engaged to form the splicing seam. When the side plates 2a and 2b have the grooves and protrusions, the side plates 2a and 2b are no longer a standard trapezoid. Only the edges of the side plates 2a and 2b on the top surface and the bottom surface of the collimator body 1 are straight edges and other opposite edges are serrated due to disposal of protrusions.

With continued reference to FIG. 6 and in combination with FIG. 5, in an implementation, the collimator body 1 is shaped like a square frustum and the splicing seam is located at a lateral edge of the collimator body 1. In a case that there are at least two side plates, for the two adjacent side plates 2a and 2b, a width of the protrusions of one side plate is equal to a thickness of the other side plate to ensure the protrusions of one side plate are located in the grooves of the other side plate. As shown in FIG. 5, the width W of the protrusion 21a of the side plate 2a is equal to the thickness of the side plate 2b. When there is only one side plate surrounding the collimator body and the splicing seam is located at the lateral edge of the collimator body 1, the width of the protrusions is equal to the thickness of the side plate.

Figure 8A:
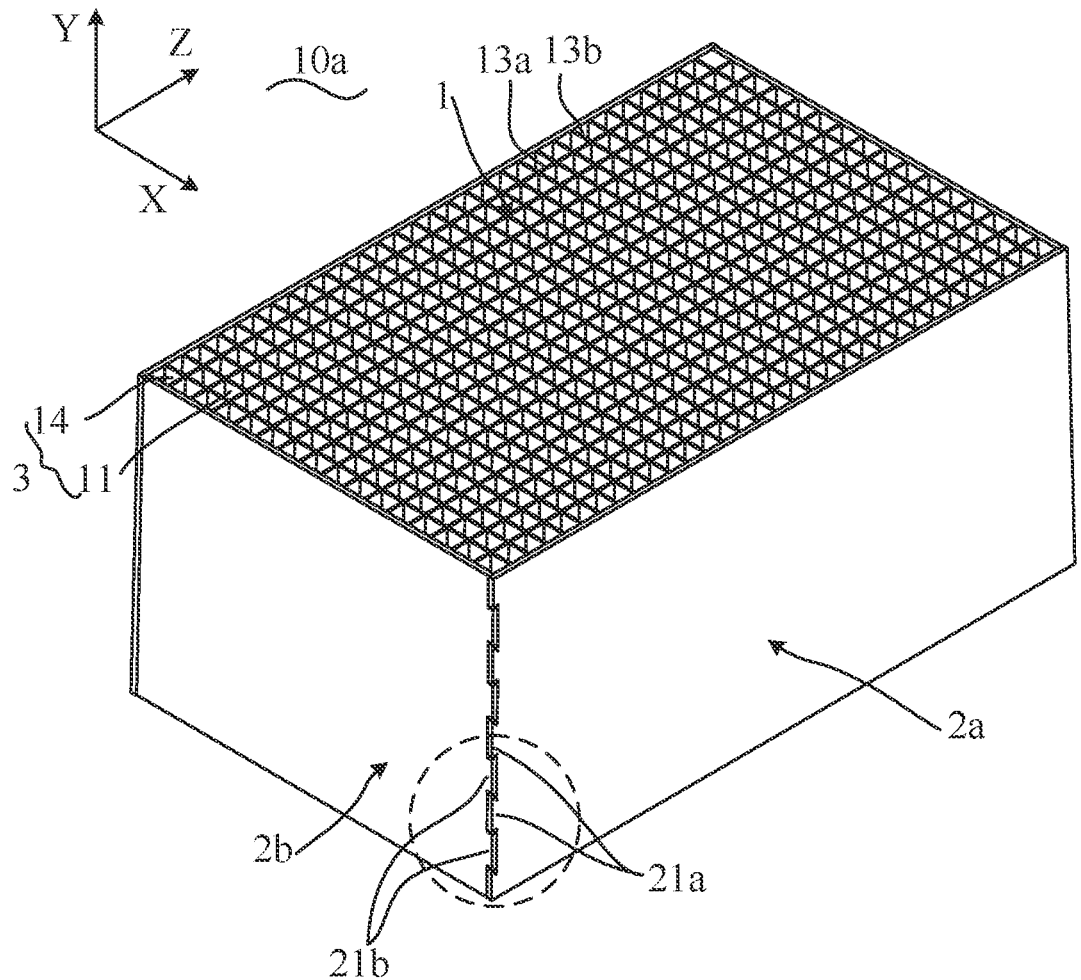
FIG. 8A is a structural schematic diagram of a collimator according to an example of the present disclosure.
Figure 8B:
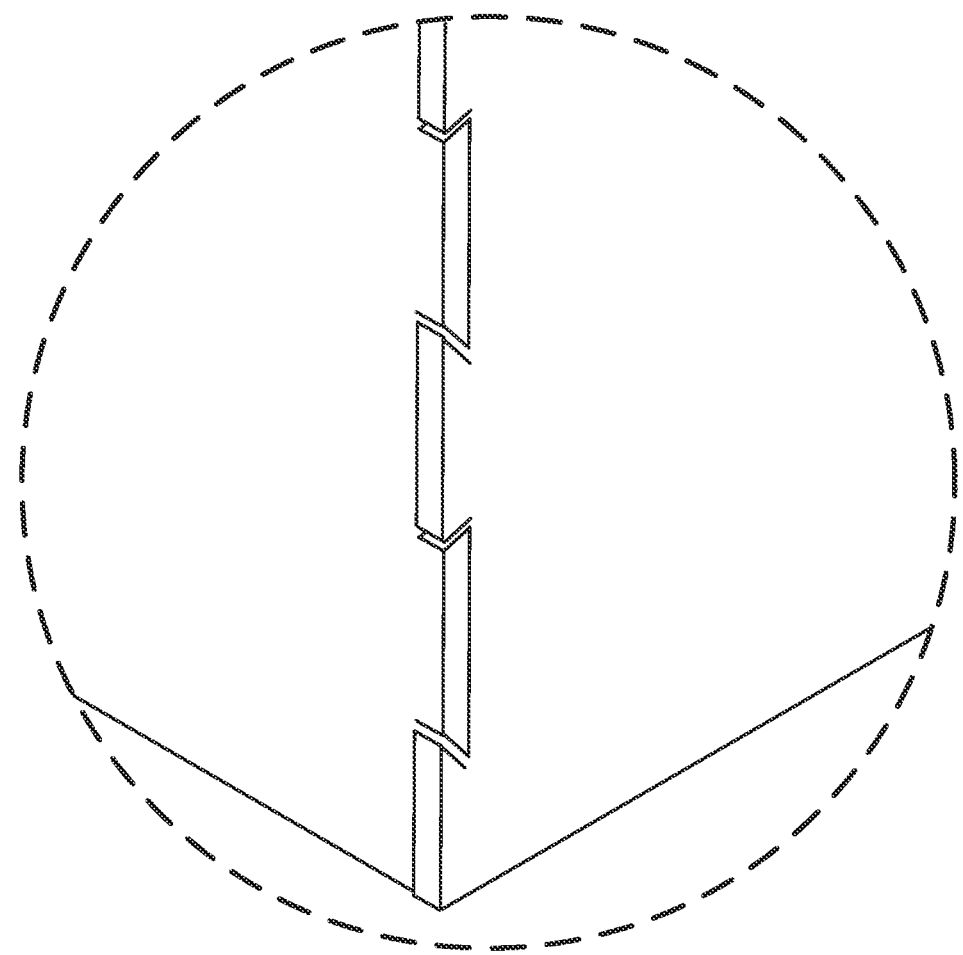
FIG. 8B is an enlarged view of a part of the collimator encircled by broken line in FIG. 8A.

In a further implementation, the protrusions 21a and 21b are square and the grooves formed between the adjacent protrusions are also square. In a further implementation, to ensure better positioning effect and better mutual supporting effect of the side plates, and thus better accuracy and more stable structure of the collimator, when the splicing seam is located at a lateral edge of the collimator body 1 as shown in FIGS. 8A and 8B, projections of the protrusions of one side plate on a plane where the side plate is located are trapezoidal and the grooves formed between the adjacent protrusions are also trapezoidal, while projections of the protrusions of the other adjacent side plate on a plane perpendicular to the other side plate are trapezoidal and thus the protrusions of the two adjacent side plates can be spliced together complementarily.

Figure 7:
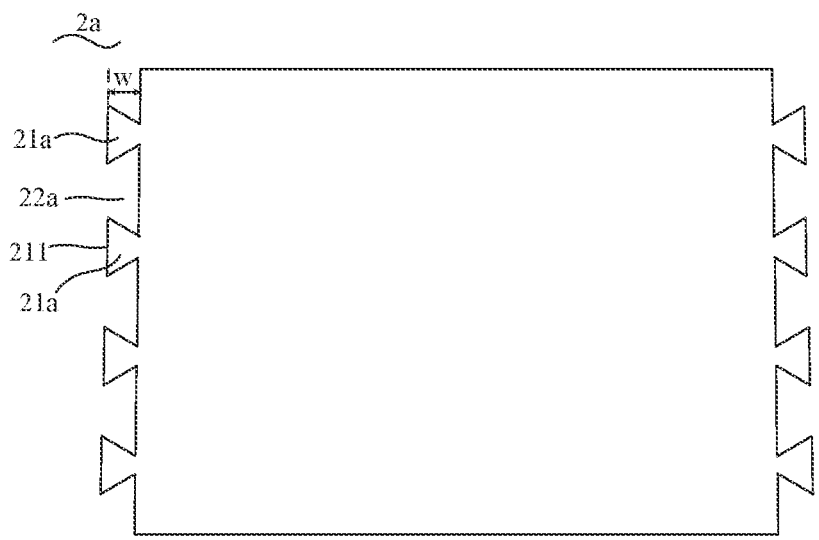
FIG. 7 is a structural schematic diagram of a side plate according to an example of the present disclosure.

In a further implementation, in a case that the projection of each of the protrusions of one side plate on the plane where the side plate is located is trapezoidal, a longer base of the trapezoid is located at the outermost side of the side plate. In this way, the protrusions of adjacent two side plates are mutually engaged to realize better mutual supporting effect. For example, in FIG. 7, a longer base 211 of the protrusion 21a is located at the outermost side of the side plate 2a. Although the manner of disposing the protrusions in a case that splicing is to be performed in the Z and X directions is described in combination with FIGS. 6 and 8A-B as above, the protrusions may also be disposed for the case that splicing is performed only along the X direction where the protrusions along the Z directions are formed on the edges of the side plates 2a by cutting process and the protrusions along the X direction are formed by 3D printing technology. In this case, the side plates 2b and the collimator body 1 are jointly formed by 3D printing technology. Taking FIG. 6 as a reference, the sides of the collimator in the X direction are provided with the openings 12, and the protrusions formed together with the collimator body 1 are equivalent to the protrusions 21b of the side plates 2b which are located on the opposite ends of the sides of the collimator in the X direction. Namely, each of the two opposite sides of the collimator body 1 includes the openings 12, protrusions located at the opposite ends of the side and grooves formed between the protrusions. Two side plates are disposed, protrusions are disposed at intervals on opposite edges of each side plate and the protrusions of each side plate are located in the grooves of the collimator body 1 so that the protrusions of the side plates and the protrusions of the collimator body 1 are alternately arranged.

FIG. 6 shows that splicing seams formed by protrusions alternately distributed are located at lateral edges when the collimator body 1 is shaped like square frustum and openings 12 are formed on the four sides. Splicing seams formed by protrusions alternately distributed can also be located at the lateral edges when two or three sides of the collimator body 1 are provided with the openings 12. A splicing seam formed by two adjacent side plates can also be located at the lateral edge when at least two sides of the collimator body 1 are provided with the openings 12 and no protrusion is disposed on the side plates. For example, in a case of at least two side plates shown in FIGS. 2 and 12, a splicing seam formed by adjacent side plates may be located at the lateral edge. In a case of only one side plate surrounding the collimator body, a splicing seam formed by opposite edges of the side plate may also be located at the lateral edge. In other implementations, the splicing seam may not be located at the lateral edge, that is, the lateral edge and the splicing seam can be spaced. In the above implementation, the splicing difficulty is reduced by having the splicing seam not located at the lateral edge. The following descriptions are related to one implementation where the splicing seam and the lateral edge are separated.

In one implementation, as shown in FIGS. 9 and 10, in a case that four sides of the collimator body 1 are all provided with the openings 12, only one side plate 2c is disposed and the splicing seam 26c formed by opposite edges of the side plate 2c is not provided at a lateral edge of the collimator body 1. FIGS. 9 and 10 show a straight splicing seam formed by opposite edges of the side plate 2c. A splicing seam formed by alternately-distributed protrusions can still be spaced from a lateral edge of the collimator body 1. In this case, the straight splicing seam 26c shown in FIGS. 9 and 10 is replaced with a serrated line formed by alternately-distributed protrusions, where the protrusions may be trapezoidal or square.

The above implementations can be combined. In a case that at least two side plates are disposed and the openings 12 are formed on at least two adjacent sides of the collimator body 1, the splicing seam of adjacent side plates and the lateral edge can be spaced, which can be achieved not only by the implementation that the one or more side plates include a trapezoidal side plate, a side plate with a U-shaped section, a side plate with an L-shaped section, or a combination thereof according to the number of sides of the collimator body 1 where openings 12 are disposed and the splicing seam is formed by alternately-distributed protrusions, but also by the implementation that the splicing seam is formed by the side plates in another manner or in another shape.

In a further implementation, when the splicing seam of adjacent side plates is spaced from the lateral edge, the projections of the protrusions 21a and 21b on the planes where the corresponding sides plates are located are trapezoidal or square, and the projections of the grooves formed between adjacent protrusions on the planes where the corresponding side plates are located are also trapezoidal or square. In a further implementation, when the projections of the protrusions on the planes where the corresponding side plates are located are trapezoidal, the longer bases of the trapezoids are located at the outermost side of the corresponding side plates.

In a case where two or three sides of the collimator body 1 are provided with the openings 12, the remaining one or two sides without the openings 12 are integrally formed with the collimator body, edges of the one or two sides without the openings 12 may be provided with protrusions and correspondingly respective edges of the side plates connecting with the one or two sides may also be provided with protrusions; alternatively, the edges of the one or two sides without openings 12 are not provided with protrusions and correspondingly respective edges of the side plates connecting with the one or two sides also may not be provided with protrusions.

In some implementations, the non-3D printing technology may be any technology which can form the side plates 2a, 2b and 2c with thicknesses smaller than the thicknesses of the body side walls 13a and 13b. The technology can include rolling process or sheet metal bending process. For example, in a case of trapezoidal side plates, the side plates may be formed with high X-ray attenuation material such as tungsten or molybdenum by rolling process; or, by cutting into a desired shape after the rolling process, for example, cutting to form the protrusions so as to manufacture the side plates 2a in FIG. 5 and the side plates 2a and 2b in FIGS. 2 and 6; or by the sheet metal bending process to manufacture the side plates 2c in FIGS. 9 and 10. In a case that the one or more side plates are formed by the sheet metal bending process, fewer splicing seams (for example, only one splicing seam is formed in FIGS. 9 and 10) and less X-ray leakage are achieved.

In some implementations, the 3D printing technology may be any technology which can form a 3D structure. For example, the 3D printing technology can include Fused Deposition Modeling (FDM) or Fused Filament Fabrication (FFF), stereolithography (SLA), digital light processing (DLP), selective laser sintering (SLS), material jetting (MJ), drop on demand (DOD), sand binder jetting, metal binder jetting, direct metal laser sintering (DMLS) and selective laser melting (SLM), electron beam melting (EBM), or any other suitable additive manufacturing (AM) technology.

Figure 13:
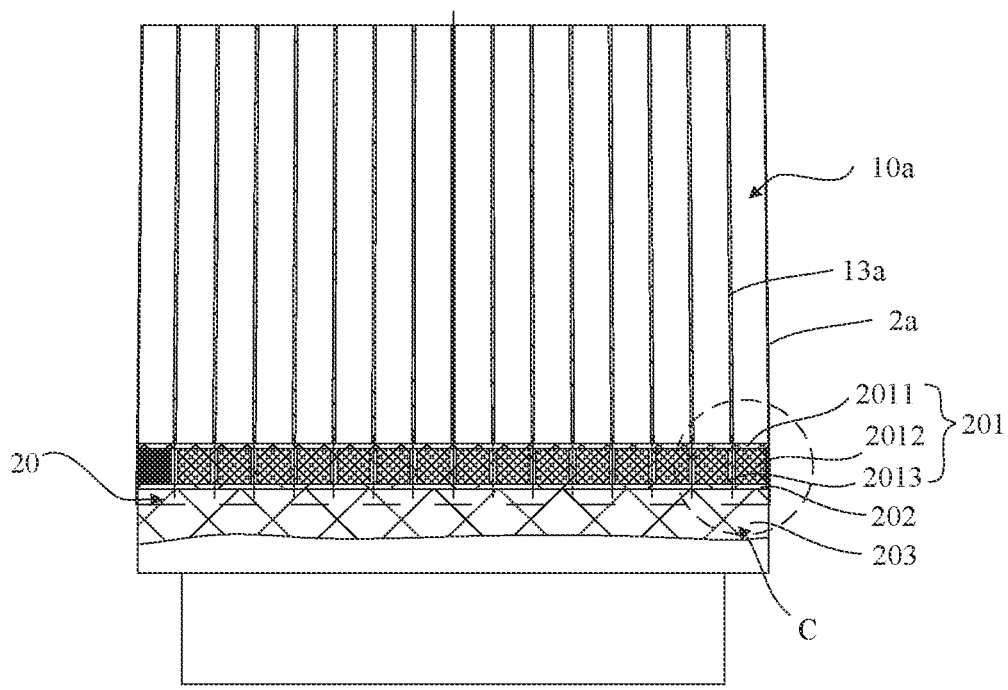
FIG. 13 is a sectional view taken along a B-B line of FIG. 12.
Figure 14:
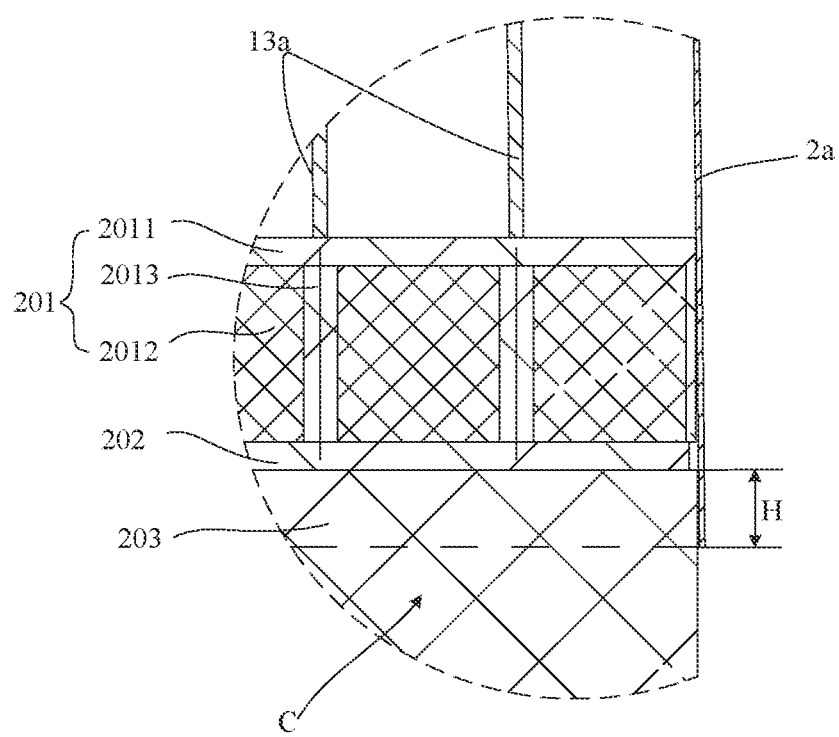
FIG. 14 is a partial enlarged view of portion C shown in FIG. 13.

The present disclosure further provides an X-ray detector system including a plurality of detector sub-modules and a plurality of collimators, for example, the detector sub-module 20 and the X-ray collimator 10a shown in FIGS. 12-14, where one X-ray collimator (e.g., the X-ray collimator 10a) is mounted on one detector sub-module (e.g., the detector sub-module 20), and the plurality of X-ray collimators and the plurality of detector sub-modules are spliced along X and Z directions so that the collimators are arranged in an array. The detector sub-modules and the collimators may be spliced only along the X direction. The detector sub-module 20 shown in FIGS. 13 and 14 includes a scintillator array 201, a photodiode array 202 and a ceramic substrate 203. The scintillator array 201 includes a reflective layer 2011, scintillator pixels 2012 and channels 2013 between the scintillator pixels 2012. The bottom surface of the collimator body 1 and an upper surface of the scintillator array 201 of the detector sub-module 20 are bonded together by adhesive. Further, the body side walls 13a of the collimator body 1 in the X direction are located on the reflective layer 201 and above the channels 2013 respectively.

In some implementations, the height of the side plates 2a, 2b or 2c is greater than the height of the collimator body 1. After the X-ray collimator is mounted on the detector sub-module 20, the side plates 2a, 2b or 2c block the detector sub-module 20 at least partially, for example, block side surfaces of the scintillator array 201 and the photodiode array 202. In this way, devices in the detector sub-module 20 can be protected against scratch and the side plates 2a, 2b or 2c can also provide shielding effect, thereby improving signal quality. As shown in FIG. 14, the height of the side plate 2a can be greater than the height of the collimator body 1 by H and this excess part with a height of H blocks the side surfaces of the scintillator array 201 and the photodiode array 202.

Further, implementations of the present disclosure provide a computed tomography (CT) device, including a bulb tube emitting X rays and any one detector system described above. Collimators of the detector system perform collimation for the X rays.

The collimator with the above structure can be not only applicable to a detector module adopting a scintillator array but also to a detector module capable of directly converting X rays into electrical signals by using CZT crystals and the like.

The above descriptions are merely preferred examples of the present disclosure and are not intended to limit the present disclosure in any form. Although the present disclosure is described with the preferred examples as above, these preferred examples are not used to limit the present disclosure. Any simple corrections, equivalent changes or modifications made to the present disclosure by those skilled in the art based on the technical essence of the present disclosure without departing the scope of the technical solutions of the present disclosure shall all fall within the scope of protection of the present disclosure.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

The terms used in the present disclosure are for the purpose of describing particular examples only, and are not intended to limit the present disclosure. The singular forms such as "a", "said", and "the" used in the present disclosure and the appended claims are also intended to include plurality, unless clearly indicated otherwise in the context. As used herein, the terms "a" and "an" are intended to denote at least one of a particular element, the term "includes" means includes but not limited to, the term "including" means including but not limited to, and the term "based on" means based at least in part on.

It should be understood that the terms such as "first" and "second" used in the present disclosure and the appended claims do not represent any sequence, number or importance but distinguish different components. Likewise, the terms such as "one" and "a" also do not represent any number but represent presence of at least one; "a plurality" represents the number of two or more. Unless otherwise indicated, the terms such as "front" "rear", "lower" and "upper" are used only for ease of descriptions and are not limited to one position or one spatial orientation. Terms such as "including" or "containing" mean that the element or article appearing before "including" or "containing" includes those elements or articles or equivalents enumerated after "including" or "containing" and does not preclude any other elements or articles.

Detailed descriptions are made to the examples of the present disclosure below in combination with accompanying drawings. In a case of no conflict, the examples and the features in the examples described above may be supplemented or combined mutually.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

What is claimed is:

1. An X-ray collimator comprising:
   a collimator body formed by three-dimensional (3D) printing; and
   one or more side plates formed by non-3D printing,
   wherein the collimator body comprises:
      a plurality of first through holes,
      a plurality of body side walls, and
      a plurality of openings located on at least one side of the collimator body,
      wherein the plurality of first through holes and the plurality of openings are enclosed by respective body side walls, extend through the collimator body, and are arranged in an array,
   wherein the one or more side plates have a thickness smaller than a thickness of the body side walls,
   wherein the one or more side plates are connected with the at least one side of the collimator body to constitute a plurality of second through holes together with the plurality of openings, the first through holes and the second through holes constituting a plurality of through holes of the X-ray collimator, and
   wherein each through hole of the plurality of through holes has a square-frustum-like shape with extension lines of four lateral edges intersecting at a focus of an emission source of X-rays, such that the X-rays pass through the through hole.

2. The X-ray collimator according to claim 1, wherein:
   the one or more side plates comprise one or more trapezoidal side plates, one or more side plates with a U-shaped section, one or more side plates with an L-shaped section, or a combination thereof according to a number of sides of the collimator body on which the openings are disposed, and the U-shaped section or the L-shaped section is parallel to a top surface of the collimator body, or
   four sides of the collimator body are provided with the openings and the one or more side plates comprise one side plate.

3. The X-ray collimator according to claim 1, wherein:
   the openings are disposed on at least two adjacent sides of the collimator body, and at least two side plates adjacent to each other are disposed; for each two adjacent side plates, protrusions are disposed at intervals on joining edges of the two adjacent side plates, grooves are formed between adjacent protrusions, and protrusions on an edge of one of the two adjacent side plates are located in grooves of a joining edge of the other one of the two adjacent side plates, and the protrusions of the two adjacent side plates are alternately distributed to form a splicing seam, or
   four sides of the collimator body are provided with the openings, the one or more side plates comprise one side plate, protrusions are disposed on opposite edges of the side plate, grooves are formed between adjacent protrusions, protrusions of one of the opposite edges are located in grooves of the other one of the opposite edges, and the protrusions of the opposite edges are alternately distributed to form a splicing seam, or
   two opposite sides of the collimator body are provided with the openings, protrusions located at respective two opposite ends of the two opposite sides and grooves located between the protrusions, the one or more side plates comprise two side plates with protrusions disposed at intervals on respective two opposite edges of the two side plates, protrusions of each of the two side plates are located in the grooves of the collimator body, and the protrusions of the two side plates and the protrusions of the collimator body are alternately arranged.

4. The X-ray collimator according to claim 3, wherein each of the protrusions has a trapezoid-like shape or a square-like shape.

5. The X-ray collimator according to claim 3, wherein the collimator body has a square-frustum-like shape, and the splicing seam is located at a lateral edge of the collimator body, and
   wherein the one or more side plates comprise:
      at least two side plates, wherein, for each two adjacent side plates, a width of protrusions of an edge of one of the two adjacent side plates is equal to a thickness of the other one of the two adjacent side plates with an edge joined with the edge of the one of the two adjacent side plates, or only one side plate, wherein the width of the protrusions is equal to the thickness of the side plate.

6. The X-ray collimator according to claim 5, wherein each of the protrusions has a trapezoid-like shape or a square-like shape.

7. The X-ray collimator according to claim 3, wherein the collimator body has a square-frustum-like shape, and the splicing seam and a lateral edge of the collimator body are spaced.

8. The X-ray collimator according to claim 7, wherein each of the protrusions has a trapezoid-like shape or a square-like shape.

9. The X-ray collimator according to claim 8, wherein each of the protrusions has the trapezoid-like shape, and longer bases of the protrusions are located at an outermost side of the one or more side plates.

10. The X-ray collimator according to claim 1, wherein the thickness of the one or more side plates is equal to or smaller than ½ of the thickness of the body side walls.

11. The X-ray collimator according to claim 1, wherein a height of the one or more side plates is greater than a height of the collimator body, and
wherein, when the X-ray collimator is mounted on a detector sub-module, the one or more side plates block at least part of the detector sub-module.

12. The X-ray collimator according to claim 1, wherein the thickness of each of the body side walls decreases gradually from a bottom surface of the collimator body to a top surface of the collimator body.

13. The X-ray collimator according to claim 1, wherein the non-3D printing comprises rolling or sheet metal bending.

14. An X-ray detector system comprising:
a plurality of detector sub-modules; and
a plurality of X-ray collimators,
wherein each of the plurality of X-ray collimators is mounted on a different corresponding detector sub-module of the plurality of detector sub-modules, and the plurality of X-ray collimators and the plurality of detector sub-modules are spliced along at least one of a first direction or a second direction of the X-ray detector system, and
wherein each of the X-ray collimators comprises:
a collimator body formed by three-dimensional (3D) printing; and
one or more side plates formed by non-3D printing,
wherein the collimator body comprises:
a plurality of first through holes,
a plurality of body side walls, and
a plurality of openings located on at least one side of the collimator body,
wherein the plurality of first through holes and the plurality of openings are enclosed by respective body side walls, extend through the collimator body, and are arranged in an array,
wherein the one or more side plates have a thickness smaller than a thickness of the body side walls,
wherein the one or more side plates are connected with the at least one side of the collimator body to constitute a plurality of second through holes together with the plurality of openings, the first through holes and the second through holes constituting a plurality of through holes of the X-ray collimator, and wherein each through hole of the plurality of through holes has a square-frustum-like shape with extension lines of four lateral edges intersecting at a focus of an emission source of X-rays, such that the X-rays pass through the through hole.

15. The X-ray detector system according to claim 14, wherein, for each of the X-ray collimators,
the openings are disposed on at least two adjacent sides of the collimator body, and at least two side plates adjacent to each other are disposed; for each two adjacent side plates, protrusions are disposed at intervals on joining edges of the two adjacent side plates, grooves are formed between adjacent protrusions, and protrusions on an edge of one of the two adjacent side plates are located in grooves of a joining edge of the other one of the two adjacent side plates, and the protrusions of the two adjacent side plates are alternately distributed to form a splicing seam, or
four sides of the collimator body are provided with the openings, the one or more side plates comprise one side plate, protrusions are disposed on opposite edges of the side plate, grooves are formed between adjacent protrusions, protrusions of one of the opposite edges are located in grooves of the other one of the opposite edges, and the protrusions of the opposite edges are alternately distributed to form a splicing seam, or
two opposite sides of the collimator body are provided with the openings, protrusions located at respective two opposite ends of the two opposite sides and grooves located between the protrusions, the one or more side plates comprise two side plates with protrusions disposed at intervals on respective two opposite edges of the two side plates, protrusions of each of the two side plates are located in the grooves of the collimator body, and the protrusions of the two side plates and the protrusions of the collimator body are alternately arranged.

16. The X-ray detector system according to claim 15, wherein the collimator body has a square-frustum-like shape, and the splicing seam is located at a lateral edge of the collimator body, and
wherein the one or more side plates comprise:
at least two side plates, wherein, for each two adjacent side plates, a width of protrusions of an edge of one of the two adjacent side plates is equal to a thickness of the other one of the two adjacent side plates with an edge joined with the edge of the one of the two adjacent side plates, or
only one side plate, wherein the width of the protrusions is equal to the thickness of the side plate.

17. The X-ray detector system according to claim 15, wherein the collimator body has a square-frustum-like shape, and the splicing seam and a lateral edge of the collimator body are spaced.

18. The X-ray detector system according to claim 14, wherein the thickness of the one or more side plates is equal to or smaller than ½ of the thickness of the body side walls.

19. The X-ray detector system according to claim 14, wherein, for each of the X-ray collimators, a height of the one or more side plates is greater than a height of the collimator body, and
wherein, when the X-ray collimator is mounted on a corresponding detector sub-module, the one or more side plates block at least part of the detector sub-module.

20. A computed tomography (CT) device comprising:
a bulb tube emitting X-rays; and a X-ray detector system,
wherein the X-ray detector system comprises:
- a plurality of detector sub-modules; and
- a plurality of X-ray collimators configured to collimate the X-rays,
- wherein each of the plurality of X-ray collimators is mounted on a different corresponding detector sub-module of the plurality of detector sub-modules, and the plurality of X-ray collimators and the plurality of detector sub-modules are spliced along at least one of a first direction or a second direction of the X-ray detector system, and
- wherein each of the X-ray collimators comprises:
  - a collimator body formed by three-dimensional (3D) printing; and
  - one or more side plates formed by non-3D printing,
- wherein the collimator body comprises:
  - a plurality of first through holes,
  - a plurality of body side walls, and
  - a plurality of openings located on at least one side of the collimator body,
- wherein the plurality of first through holes and the plurality of openings are enclosed by respective body side walls, extend through the collimator body, and are arranged in an array,
- wherein the one or more side plates have a thickness smaller than a thickness of the body side walls,
- wherein the one or more side plates are connected with the at least one side of the collimator body to constitute a plurality of second through holes together with the plurality of openings, the first through holes and the second through holes constituting a plurality of through holes of the X-ray collimator, and
- wherein each through hole of the plurality of through holes has a square-frustum-like shape with extension lines of four lateral edges intersecting at a focus of an emission source of X-rays, such that the X-rays pass through the through hole.

* * * * *